United States Patent [19]

Mittleman

[11] 4,248,401
[45] Feb. 3, 1981

[54] PLASTIC SLIDE CLAMP FOR TUBING
[75] Inventor: Herbert Mittleman, Deerfield, Ill.
[73] Assignee: Baxter Travenol Laboratories, Inc., Deerfield, Ill.
[21] Appl. No.: 36,624
[22] Filed: May 7, 1979
[51] Int. Cl.³ .............................................. F16K 7/04
[52] U.S. Cl. ........................................ 251/7; 24/130; 24/264
[58] Field of Search ................ 128/346; 251/4, 7, 8; 24/130, 264

[56] References Cited

U.S. PATENT DOCUMENTS

| D. 200,729 | 3/1965 | Coanda et al. | D54/13 |
| D. 230,729 | 3/1974 | Zeddies | D16/1 R |
| D. 233,312 | 10/1974 | Lock | D8/259 |
| 420,166 | 1/1890 | Phelps | 24/264 |
| 420,419 | 1/1890 | Smith | 24/264 |
| 2,092,400 | 9/1937 | Miller | 251/7 |
| 3,316,935 | 5/1967 | Kaiser et al. | 24/130 X |
| 3,357,674 | 12/1967 | Coanda et al. | 251/7 |
| 3,374,509 | 3/1968 | Logan et al. | 251/4 X |
| 3,555,624 | 1/1971 | Koehn | 24/264 |
| 4,193,574 | 3/1980 | Barnes et al. | 251/1 A |

OTHER PUBLICATIONS

Travenol Drawings: BL-BM9122; BL-AP10104 and BL-BP1027C, Travenol Laboratories, Inc., Deerfield, Ill. 60015.

Primary Examiner—Martin P. Schwadron
Assistant Examiner—Richard Gerard
Attorney, Agent, or Firm—John P. Kirby, Jr.; John A. Caruso; Kirk M. McInerney

[57] ABSTRACT

A plastic slide clamp for tubing is provided which includes a slightly bowed configuration to compensate for the phenomenon of cold flow when plastic tubing is crimped shut by the clamp. In one embodiment, the clamp is provided with an insert member of low friction surface properties which surrounds the crimping slot.

11 Claims, 7 Drawing Figures

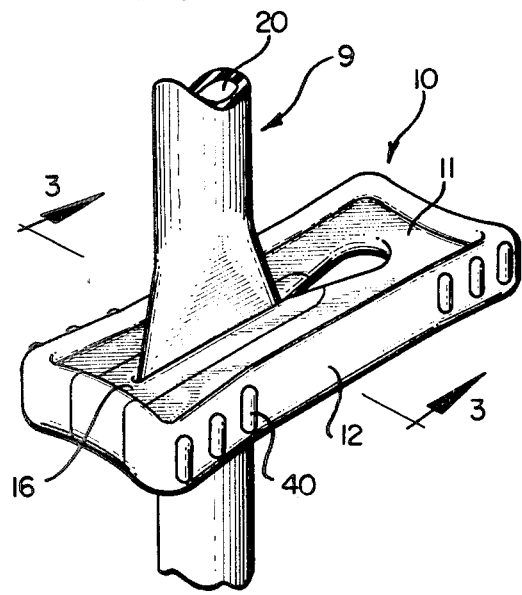
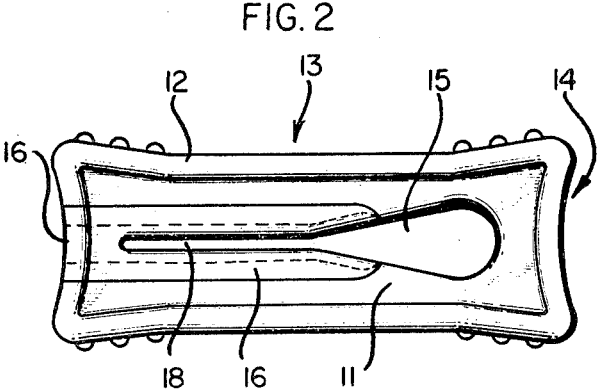
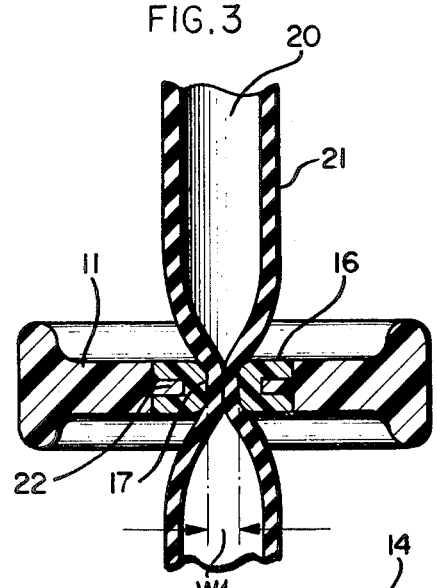
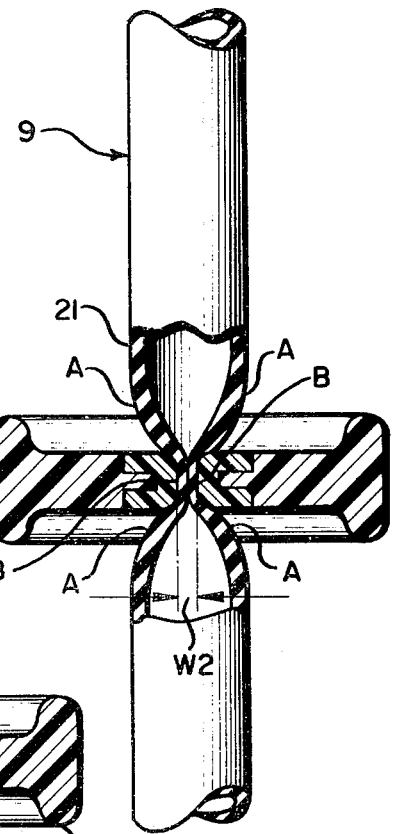
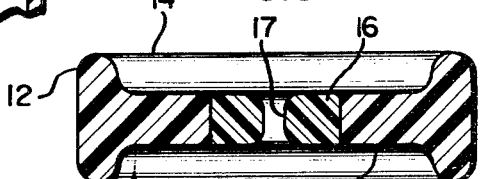
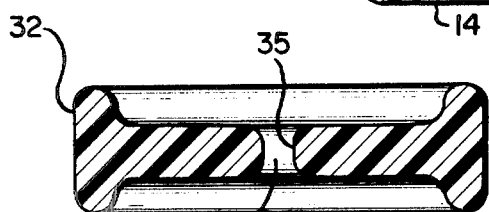
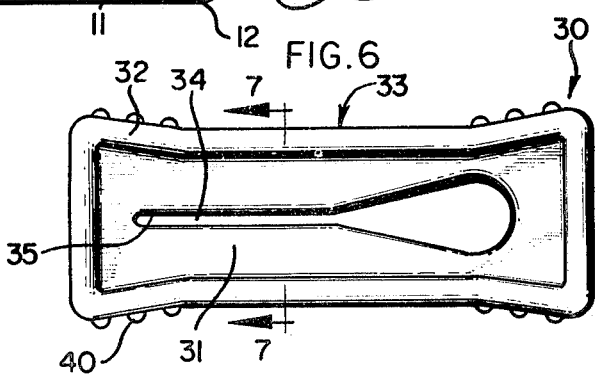

PLASTIC SLIDE CLAMP FOR TUBING

BACKGROUND OF THE INVENTION

This invention relates generally to tubing clamps and particularly to a slide clamp which is employed to open and close the fluid passageway of flexible tubing.

Several types of slide clamps have been proposed in the prior art. For example, slide clamps fabricated from metal suffer numerous disadvantages, which principally include sharp edges which tend to cut both tubing and the person manipulating the clamp. Metal slide clamps also have a tendency to scissor or transversely twist from the desired perpendicular relationship to an undesirable parallel relationship with the tubing when the user slides those clamps open and closed. Consequently, metal slide clamps have proved to be impractical for repeated opening and closing of resilient vinyl, plastic or rubber tubing, both to the user during manipulation of the clamp and to the tubing itself.

Slide clamps fabricated from a plastic material have been proposed in an attempt to reduce the deleterious effects both to the tubing and to the user which are present with metal slide clamps, as described above. Although these clamps did reduce the hazards of cutting and scratching presented to a doctor or technician manipulating the clamp, it was found that large frictional forces made the manipulation of the clamp particularly difficult when the tubing is crimped shut into a narrow slot and reversably uncrimped and opened. Moreover, the tubing wall is oftentimes ruptured when these plastic clamps were employed to crimp the tubing closed.

When plastic tubing is transversely compressed into a narrow slot by a plastic or metal slide clamp, the constant pressure from the clamp causes the tubing wall to undergo "cold flow" or "plastic creep" in the immediate vicinity where the tubing is crimped. This phenomenon begins to occur within minutes from the time when the tubing is first crimped. After a short period, the cold flow of the tubing wall away from the crimped area results in an ineffective and weak closure of the tubing. U.S. Pat. No. 3,357,674 discloses a plastic slide clamp which is unable to compensate for the phenomenon of cold flow and is so difficult for the user to manipulate, that a thumb ring must be provided.

Overcoming the physical phenomenon of cold flow has posed great difficulties in disposable and inexpensive slide clamps heretofore proposed. The unreliable sealing characteristics and inability to compensate for cold flow has contributed to numerous hospital patient accidents. Cold flow produces an ineffective seal and may lead to "fluid flooding" which results from ineffective slide clamps proposed to date which are unable to compensate for unreliable sealing characteristics attributable to cold flow.

A plastic slide clamp has been proposed by Travenol Laboratories, Inc. which eliminates some of the problems present in prior clamps. That clamp has been employed for larger diameter rubber tubing having an internal diameter of greater than about 0.225 inches. For larger diameter tubing, the Travenol clamp reduces the tendency to scissor and the tendency to rupture the tubing wall present with prior proposed plastic slide clamps. However, the Travenol clamp suffers from the disadvantages described above when employed with plastic tubing having an internal diameter of less than about 0.225 inches.

The need is apparent for a plastic slide clamp which can be easily manufactured in different sizes for a variety of tubing diameters, is less difficult to manipulate, and is able to compensate for cold flow and maintain the tubing in a closed position to eliminate the dangers of fluid flooding.

SUMMARY OF THE INVENTION

An object of the present invention is to provide a slide clamp for tubing which is easily manipulable by the user and inexpensive to manufacture, resulting in an effective, disposable clamp.

An additional object of the present invention is to provide a plastic slide clamp which may be employed to repeatedly open and close fluid tubing, particularly plastic tubing without deleteriously affecting the tubing walls.

A further object is to provide a plastic slide clamp for tubing which compensates for "cold flow" or "plastic creep" and provides for effectively stopping fluid flow within the tubing for extended periods of time.

BRIEF DESCRIPTION OF THE FIGURES

The above and other objects of the invention are more particularly set forth in the following detailed description and in the accompanying drawings of which:

FIG. 1 is a perspective view of an embodiment of the invention shown in use with a section of plastic tubing in the closed position;

FIG. 2 is a top view of the embodiment shown in FIG. 1;

FIG. 3 is a sectional view of FIG. 1 along line 3—3 depicting the tubing as it would appear immediately after crimping the tubing; before cold flow has begun;

FIG. 4 is the same view as FIG. 3 depicting the phenomenon of cold flow after an interval of time for which the tubing has been crimped;

FIG. 5 is a cross sectional view of an embodiment of the invention depicting an insert;

FIG. 6 is a top view of another embodiment of the invention without an insert;

FIG. 7 is a sectional view of FIG. 6 along line 7—7.

DESCRIPTION OF THE PREFERRED EMBODIMENT

The present invention provides for a slide clamp with and without an insert which is adapted to repeatedly open and close the fluid passageway of tubing, particularly plastic tubing employed in hospitals. Plastic tubing is widely used in hospitals to provide a conduit between a container of fluid at one end of the tube and a patient. The present invention provides a slide clamp which can be employed to effectively interrupt the fluid flow within the tubing as a result of the configuration of the clamp itself and its crimping surfaces.

Referring now to FIGS. 1 and 2, there is shown a plastic slide clamp in use with a length of tubing 9, depicted as an elongated member, embodying various aspects of the invention. As shwon, the elongated member or the clamp 10 includes a center platform 11 and an outer border 12 which is of somewhat greater thickness both above and below the center platform 11 and thereby defining longitudinal sides 13 running the length of clamp as well as transverse ends 14.

The center platform 11 of clamp 10 has a slot which is dimensioned at one end to allow the tubing to be inserted through the clamp and to remain open as shown generally be the tear-shaped portion 15 of the slot. As shown in FIGS. 1 and 2, the tear-shaped portion 15 of the slot in the center platform 11 is adapted to receive an insert member 16. The insert 16 is secured within the tear-shaped slot 15 in the center platform 11 and serves generally as the crimping section of the clamp 10. As depicted in FIGS. 2 and 3, the crimping section of insert 16 has crimping surfaces 17, generally perpendicular to the plane of the center platform 11, which define an elongated crimping slot 18 having a generally parallel configuration which terminates near the end of the platform 11 opposite the tear-shaped portion 15.

The insert 16 is dimensioned and positioned within the center platform 11 to form the crimping slot 18 for a length of tubing 9 as shown generally with the tubing in the crimped closed position in FIGS. 1, 3 and 4. FIGS. 3 and 4 more clearly illustrate the function of crimping surfaces 17 when the clamp is manipulated to crimp or close the fluid passageway 20 of the tubing. The insert is fabricated from a material having low friction surface properties such as Teflon, Delrin, Kel-F, or any other suitable material. The remainder of the clamp 10 consists of a uniform, assembly of any plastic material which can be injection molded and possess good elasticity such as, for example, polypropylene, polyvinyl chloride, acrylonitrile butadiene styrene, or similar materials.

The insert 16 of a material having low friction surface properties as shown in FIGS. 1 to 5, helps to eliminate difficulty in manipulating the clamp 10. Furthermore, the lower frictional forces created by the insert 16 when the tubing 9 is crimped between surfaces 17 reduces the tendency of cutting or of substantially weakening the tubing wall 21 at the point of repeated crimping and opening of the fluid passageway 20. The embodiment of FIGS. 1 to 5 having the insert is preferred.

The clamp 10 may be used to open and close tubing fabricated from a variety of flexible materials, but is particularly advantageous when employed with, as generally referred to, plastic tubing. This type of tubing possesses a variety of advantages over other tubing materials and is widely used, particularly in the medical field. However, plastic tubing when crimped shut by a slide clamp will undergo "cold flow" or "plastic creep" after a relatively short period of time. Cold flow will generally commence within 10 to 30 minutes depending upon such factors as tubing size and material. This phenomenon of cold flow is attributed to the transverse pressure to the tubing wall, as depicted in FIG. 3, when the tubing is first positioned within the crimping surfaces 17 of crimping slot 18. The crimping surfaces 17 of insert 16 are diametrically opposed and spaced so that when the tubing 9 is crimped into the crimping slot 18, the fluid passageway 20 will be crimped shut.

After a relatively short interval, the pressure causes the tubing wall 21 in the vicinity of crimping surfaces 17 to undergo cold flow or plastic creep. As shown in FIG. 4, the cold flow of the tubing wall causes the wall to become thinner at the crimped portion B of the tubing and to become thicker at points A above and below the crimped portion B.

As shown in FIGS. 1 and 2, the outer border 12 of center platform forms longitudinal sides 13 which are bowed inwardly towards the platform 11. A similar configuration is provided for the clamp 30 of FIGS. 6 and 7 which does not have the insert 16 adapted within its center platform 31, and is fabricated from a uniform plastic material. In both of these embodiments, the longitudinal sides of the outer border are bowed inwardly to allow for an inwardly directed spring-like compression for the crimping slot. This inwardly directed spring-like compression is created when the clamps are fabricated with longitudinal sides which are bowed inwardly as a consequence of the internal stresses inherent in the fabricated plastic clamp.

The spring-like compression provided for by the inwardly bowed configuration of the clamp 10 allows for a slight expansion of the width W1 between crimping surfaces 17 when the tubing 9 is first crimped closed as shown in FIG. 3. This slight outward distention of the width W1 between crimping surfaces 17 is on the order of a few thousandths of an inch. FIG. 3 depicts a cross sectional view of the tubing 9 crimped shut by the clamp 10 as it would appear immediately after or within a relatively short period of time from when the tubing 9 is first crimped closed.

As described above, within 10 to 30 minutes the phenomenon of cold flow or plastic creep will occur as shown in FIG. 4. The inwardly directed spring-like compression provided by the clamp 10 will compensate for the tubing wall 21 having become thinner at the crimped portions B. The spring-like compression has caused the width W2 between crimping surfaces 17 to become slightly narrower thereby compensating for the now thinner portions B. In this manner, the clamp 10 provides an effective closure of the fluid passageway 20 of the tubing 9 for extended periods of time.

During the interval when the tubing is undergoing "cold flow" or "plastic creep", the spring-like compression causes a narrowing of the slot 18 which correspondingly compensates for the narrowing of the tubing wall 21 at the crimped portion B.

The improved slide clamp for tubing of the present invention as shown in FIGS. 1 to 5, illustrating the embodiment having the insert 16, is readily fabricated from known injection molding techniques which employ a two-step process for the molding of a plastic article consisting of two different materials. FIGS. 3 and 4 illustrate in cross section the clamp 10 that would result from a mold design which would allow for the insert 16 to be injection molded around a nipple 22 projecting from the center platform 11. FIG. 5 shows an alternate mold design which would allow for the molding of insert 16 to be within the center platform 11 in a vertical fashion in place of the nipple 22 as shown in FIGS. 3 and 4. FIGS. 1 and 2 show the clamp 10 with the molded insert 16 which terminates at the end adjacent to the crimping section as part of the outer border 12 of the center platform 11. In place of a two-step injection molding process, the insert 16 may be fabricated separately and secured to the center platform 11 by any suitable means, such as heat fusing, glueing, or the like.

As briefly described above, FIGS. 6 and 7 show another embodiment wherein the clamp 30 has a center platform 31 and outer border 32 defining inwardly bowed, longitudinal sides 33. The bowed configuration of this embodiment of the invention is important for enabling the clamp 30 to compensate for cold flow as discussed above in reference to FIGS. 3 and 4. This shape for the clamp 30 of FIGS. 6 and 7 also allows for an inwardly directed spring-like compression. The clamp 30 will slightly expand outwardly, on the order of a few thousandths of an inch, when the tubing is first crimped and will subsequently contact its crimping slot section 34 as the tubing undergoes cold flow.

In the embodiment shown in FIGS. 6 and 7, the absence of an insert of low friction surface properties which reduces frictional and shear forces during crimping, makes it preferred that the crimping slot 34 have crimping surfaces 35 with a rounded cross section as shown in FIG. 7. The rounded crimping surfaces 35 are preferred when this clamp is employed with smaller diameter plastic tubing, i.e., having an internal diameter of about 0.225 inches or less. The rounded crimping surfaces 35 are provided to alleviate the frictional forces when the clamp 30 is employed with smaller diameter, plastic tubing thereby reducing shear forces which cause the tubing wall to rupture. Consequently, repeated crimping and opening of smaller diameter tubing may be achieved without cutting the tubing wall at the point of constriction in slot 34. For example, it has been found that a sharper or an inwardly tapering crimping surface such as is present in Travenol's Medical Products Division clamp, will tend to rupture the tubing wall when employed with smaller diameter plastic tubing, i.e., less than about 0.225 inches.

To help prevent wall rupture and facilitate manipulation of the clamp 30 shown in FIGS. 6 and 7, the rounded crimping surfaces 35 may be coated in a known manner with a material having low surface friction properties such as silicon spray or any suitable material. However, this coated material on the rounded crimping surfaces 35 has a tendency to be rubbed off easily. Furthermore, the coated material may evaporate after a shelf-life of about six to nine months between the date of manufacture and first use.

The longitudinal sides 33 of the clamp 30 shown in FIGS. 6 and 7 are bowed inwardly on the order of at least a few degrees to provide sping-like compression. The clamp 30 may also be manufactured for a variety of tubing inner and outer diameters as described above for the embodiment shown in FIGS. 1 to 5.

The embodiment shown in FIGS. 6 and 7 is satisfactory for those applications wherein repeated opening and closing of the tubing is not required. However, the embodiment as shown in FIGS. 1 through 5 with the insert 14 is preferred for those situations requiring repeated opening and closing of the tubing.

The longitudinal sides 13 of the embodiment shown in FIGS. 1 to 5, as well as for those of the embodiment of FIGS. 6 and 7, are slightly bowed inwardly for at least a slope of a few degrees. The clamps 10 and 30 disclosed herein may be manufactured for use with a variety of tubing outer and inner diameters. The width of the crimping slot is within the range of plus or minus 10% of the tubing wall thickness for which the clamp will be employed and is preferably about equal to the wall thickness (depicted as element 21).

The ratio of the thickness of the outer border 12 and 32 to the thickness of the center platform 11 and 31 should be at least on the order of 2:1 for the embodiments disclosed herein. This ratio affects the spring-like compression provided for by the clamp embodiments disclosed herein and it has been found that a border to platform thickness of about 2.5:1 works well to compensate for plastic creep while remaining easy to manipulate by the user. Larger ratios will also work, but will make manipulation of the clamp correspondingly more difficult to manipulate.

The crimping slot length is at least 50% greater than the length of the crimped tubing (as depicted in FIG. 1) to insure an effective seal. Preferably, the crimping slot is twice as long as the transverse length of the tubing at the crimped section. In this manner, different size clamps may be fabricated for use with a particular tubing outer and inner diameter.

The clamp may be provided with means to assist the user in gripping the clamp when in use, as shown in the figures by horizontally, elongated protrusions 40. To further assist the user, the clamp is shown generally with rounded, transverse ends 14 in which the user's thumb may comfortably be fitted. Neither feature, however, is critical for the invention and variations of these two features will be apparent to one of ordinary skill in the art.

Although the invention has been described in terms of preferred structures, it will be apparent to one skilled in the art that obvious modifications may be made without departing from the invention. It is intended that all such modifications are included in the spirit and scope of the invention as defined herein and protected by the appended claims.

What is claimed is:

1. A plastic slide clamp for fluid tubing comprising:
an elongated member including a center platform having an outer border of greater thickness than the thickness of said center platform forming longitudinal sides and transverse ends;
a slot dimensioned and positioned within said center platform which tapers longitudinally to a narrow transverse portion and thereafter having substantially parallel sides to define a crimping slot to crimp and to close a fluid passageway of the tubing;
rounded crimping surfaces having a rounded, transverse cross section as defined by said parallel sides of said crimping slot in said center platform, for crimping the tubing in the closed position; and
a central portion of said elongated member wherein said longitudinal sides of the outer border of said center platform are not parallel to one another near said transverse ends, the configuration of said longitudinal sides and the relative thickness of said longitudinal sides and of said center platform coact to provide continuous inwardly directed spring-like compression when the tubing is crimped to thereby compensate for cold flow of the tubing,
whereby said elongated member may be easily moved transversely to the tubing to repeatedly open and close, and to effectively close the fluid passageway of the tubing over a period of time.

2. A plastic slide clamp for tubing comprising:
an elongated member of moldable material including a center platform having an outer border of greater thickness than the thickness of said center platform forming longitudinal sides and transverse ends, said center platform adapted to receive an insert member therein; and
said insert member being received within the center platform and dimensioned to define a crimping slot having low friction surface properties tapering longitudinally to a narrow transverse portion and thereafter having substantially parallel sides to crimp and to close a fluid passageway of the tubing;
whereby said elongated member may be easily moved transversely to the tubing to repeatedly open and close the fluid passageway of the tubing.

3. A plastic slide clamp for tubing according to claim 2, wherein said longitudinal sides of the outer border are not parallel to one another near said transverse ends to further define a central portion of said elongated member which is of lesser transverse width than said ends to allow for continuous spring-like compression when the clamp is in the the closed position to thereby compensate for cold flow of the tubing.

4. A plastic slide clamp for tubing according to claim 2, wherein the slot defines surfaces having a rounded, transverse cross section for crimping the tubing in the closed position.

5. A plastic slide clamp for tubing according to claim 2 wherein the moldable material of said elongated member consists of an injection moldable plastic and the insert consists of a moldable material having similar properties to either Teflon or Delrin.

6. A plastic slide clamp for tubing according to claim 2 further including a series of slight protrusions on said outer border to increase the transverse grippability of said clamp.

7. A plastic slide clamp for tubing according to claim 2, wherein said ends are inwardly arcuate to facilitate the opening and closing of the slide clamp.

8. A plastic slide clamp for tubing according to claim 2, wherein said insert is injection molded into said center platform.

9. A plastic slide clamp for tubing according to claim 2, wherein said insert is fused to said center platform by heat.

10. A plastic slide clamp for tubing according to claim 2, wherein said insert is adhesively bonded to said center platform.

11. The slide clamp of claim 1 wherein said thickness of said longitudinal sides is at least approximately twice as thick as said center platform.

* * * * *